United States Patent [19]

Baggett et al.

[11] 4,111,899

[45] Sep. 5, 1978

[54] HEAT STABILIZED THERMOPLASTIC RESINS CONTAINING COMPOUNDS WITH PHOSPHORUS TO PHOSPHORUS BONDS

[75] Inventors: Joseph M. Baggett, Freeport; George E. Ham, Lake Jackson, both of Tex.

[73] Assignee: The Dow Chemical Company, Midland, Mich.

[21] Appl. No.: 817,326

[22] Filed: Jul. 20, 1977

[51] Int. Cl.$^2$ .......................... C08K 5/50; C08K 5/52; C08K 5/53

[52] U.S. Cl. .......................... 260/45.8 R; 260/45.7 P; 260/45.9 NP; 260/927 R

[58] Field of Search ................... 260/45.8 R, 45.9 NP, 260/927 R, 45.7 P

[56] References Cited

U.S. PATENT DOCUMENTS

| | | | |
|---|---|---|---|
| 2,952,701 | 9/1960 | McConnell et al. | 260/927 R |
| 3,003,996 | 10/1961 | Newland et al. | 260/45.9 NP |
| 3,108,091 | 10/1963 | Illing et al. | 260/45.7 P |
| 3,201,369 | 8/1965 | Dell et al. | 260/45.7 P |
| 3,383,354 | 5/1968 | Prinz et al. | 260/45.9 NP |
| 3,450,670 | 6/1969 | Holoch et al. | 260/45.9 NP |
| 3,597,511 | 8/1971 | Olson et al. | 260/45.8 R |
| 3,794,615 | 2/1974 | Beverly | 260/45.7 P |
| 3,897,391 | 7/1975 | Jaquiss et al. | 260/45.7 P |
| 4,024,103 | 5/1977 | Heinrich et al. | 260/45.7 P |

Primary Examiner—Donald E. Czaja
Assistant Examiner—R. A. White
Attorney, Agent, or Firm—B. G. Colley

[57] ABSTRACT

Thermoplastic resin compositions are heat stabilized by the addition of 0.01 to 1.0 percent by weight of an organo-phosphorus compound having one of the formulas $$(R_1)(R_2) P (=X)_a - P(=X)_a (R_1)(R_2) \qquad \text{I}$$

$$(P - R_1)_n \qquad \text{II}$$

$$(R_1)(R_2) P (=X)_a - P(R_3) - P(=X)_a (R_1)(R_2) \qquad \text{III}$$

wherein $a$ is independently 0 or 1, $n$ is 3 to 6, X is oxygen or sulfur, $R_1$, $R_2$, and $R_3$ are independently dialkylamino, alkoxy, aryloxy, alkyl, aryl, alkaryl, aralkyl, or MO where M is an alkali metal, or $R_1$ and $R_2$ taken with the P atom represent a cyclic structure.

10 Claims, No Drawings

HEAT STABILIZED THERMOPLASTIC RESINS CONTAINING COMPOUNDS WITH PHOSPHORUS TO PHOSPHORUS BONDS

BACKGROUND OF THE INVENTION

This invention relates to thermoplastic resin compositions which are resistant to discoloration during molding and which comprise a thermoplastic polymer and a stabilizing amount of an organic compound containing one or more phosphorus to phosphorus bonds.

It is known from U.S. Pat. No. 2,373,670 dated Apr. 17, 1945 that phosphorus compounds of the formula

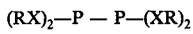

are useful film strength improvers when blended with a major amount of lubricating oils.

The compounds used in this invention are known or can be prepared from the above patent and from "Preparative Inorganic Reactions" by W. L. Jolly, Vol. 5, pages 103–156 (1968); "Chemical Reviews," Vol. 65, No. 6, pages 617–634 (1965); and "Organic Phosphorus Compounds" by G. M. Kosolapoff and L. Maier, Vol. 5, pages 1–20 (1973).

SUMMARY OF THE INVENTION

It has been found that compounds having a phosphorus to phosphorus bond are useful to stabilize thermoplastic polymers or resins from the effects of heat and/or oxygen during the molding of a blend containing the polymers and a compound having one or more P—P bonds.

More specifically, the invention relates to compositions comprising a thermoplastic polymer and a stabilizing amount of a compound having one of the formulas

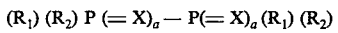

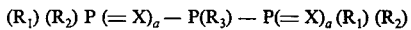

wherein $a$ is independently 0 or 1, $n$ is 3 to 6, X is oxygen or sulfur, $R_1$, $R_2$, and $R_3$ are independently dialkylamino, alkoxy, aryloxy, alkyl, aryl, alkaryl, aralkyl, or MO where M is an alkali metal, $R_1$ and $R_2$ taken with the P atom represent a cyclic structure.

A preferred species of the invention is a thermoplastic polycarbonate resin containing a compound of the formula

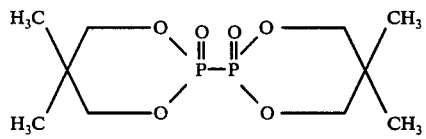

The blends or compositions of this invention are thus useful to make molded parts as in the injection molding of diverse articles such as cups, glasses, valve fittings, appliance covers, etc.

DESCRIPTION OF THE PREFERRED EMBODIMENTS

The thermoplastic resins or polymers which can be used in the compositions of this invention are illustrated by polyalkylenes such as polyethylene, polypropylene and related copolymers; polyvinyl chloride; vinyl polymers such as polystyrene and related copolymers such as styrene-butadiene-acrylonitrile copolymers; acrylic polymers such as polyacrylonitriles and poly(methylmethacrylates) and related copolymers; polyesters such as poly(ethylene terephthalates); and aromatic polycarbonates such as bisphenol A polycarbonate and copolycarbonates with diverse dihydroxy phenols.

The compounds having a P—P bond which can be used in the invention are illustrated by, and not limited to, the following:

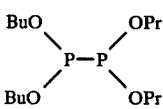

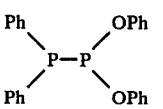

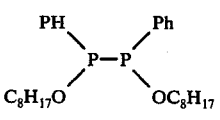

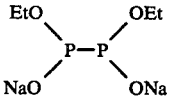

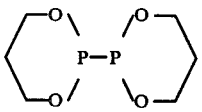

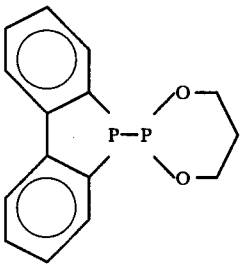

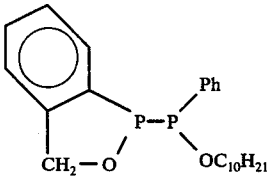

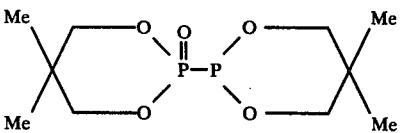

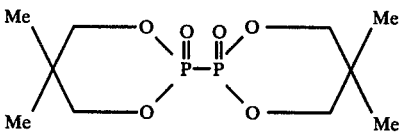

-continued

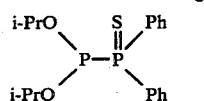

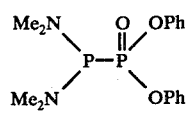

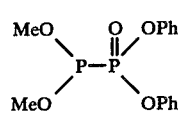

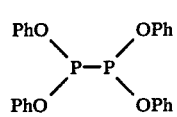

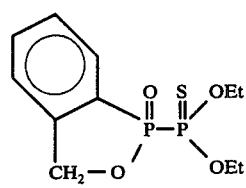

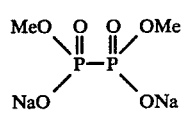

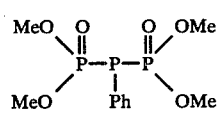

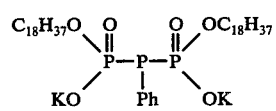

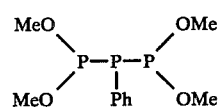

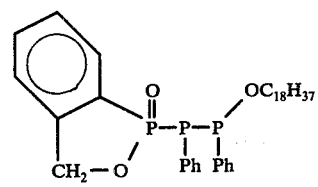

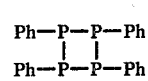

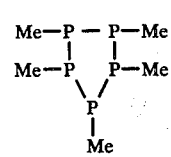

-continued

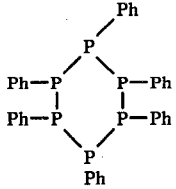

wherein
Ph signifies the phenyl group,
Me signifies the methyl group,
Et signifies the ethyl group, and
$i$-Pr signifies the isopropyl group.

For the purposes of this invention a stabilizing amount of the compounds is defined as a range from about 0.01 to about 1.0 percent by weight and preferably about 0.05 to about 0.25 based on the total weight of the polymer.

The compositions of this invention may also be blended with other conventional additives such as ultra violet light stabilizers, antioxidants, dyes and pigments.

PREPARATION I

Bis(5,5-dimethyl-2-oxo-1,3,2-Dioxaphosphorinanyl)

Into a flask fitted with stirrer, nitrogen purge, feeding funnel, thermometer, and reflux condenser were charged 50 ml of dry benzene and 4.6 grams (0.1 mole) sodium:paraffin 50:50 dispersion. The mixture was stirred about 30 minutes at room temperature with a slow nitrogen purge and then a solution containing 15 grams, (0.1 mole) of 2-hydroxy-5,5-dimethyl-1,3,2-dioxaphosphorinan dissolved in 50 ml. of dry benzene was fed in at such a rate that the temperature was kept below 30° C. The contents was stirred for 15 minutes at 25° C and then a solution of 12.0 grams (0.066 mole) of 2-chloro-2-oxo-5,5-dimethyl-1,3,2-dioxaphosphorinan dissolved in benzene (50 ml.) was fed dropwise at 5°-7° C. The reaction temperature was controlled by rate of addition and an ice acetone-water bath. After the feed was in, the reactants were stirred and digested at 25° C. for 3 hours. The contents were again cooled to 5° C. by an external source at which time 100 ml. of an aqueous 5% NaHCO$_3$ solution was added and stirred for a few minutes. The contents were transferred to a separating funnel and allowed to phase out. At the interface a solid forms. The solid was filtered off then dried. It had a melting point of 222° C. The crude product was recrystallized using CHCl$_3$: ethyl acetate (2:1), filtered then washed with water, filtered again then dried. The white needle crystals weighed 5.15 grams and had a melting point of 255° C. The product was identified by phosphorous-31 Nuclear Magnetic Resonance; Infrared; and Mass Spectroscopy and had the formula:

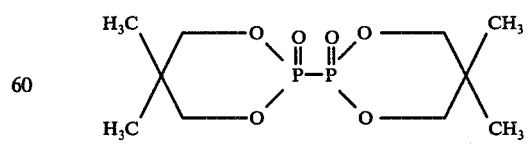

PREPARATION 2

Into a flask equipped with stirrer, nitrogen purge, thermometer, and reflux condenser were charged 175 ml. of benzene. The flask was purged with nitrogen to remove the air and then 25 ml. of benzene was distilled off to remove any trace of water. The contents were cooled to 25° C. and then with stirring 35.8 grams (0.2 mole) of dichlorophenyl phosphine was added, all at once, followed by the addition in the same manner 49.6 grams (0.4 mole) of trimethyl phosphite. The mixture was refluxed for 3 hours, cooled, and transferred to a Rinco flask where the benzene was removed by distillation using high vacuum and 90° C. temperature. The resulting product was a colorless liquid, having a weight of 53 grams, and upon standing overnight began to crystallize. The product was identified by Phosphorous 31 Nuclear Magnetic Resonance to be the compound having the formula:

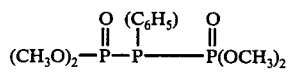

PREPARATION 3

33 grams (0.15 mole) of chlorodiphenylphosphine and 18.6 grams (0.15 mole) of trimethyl phosphite was fed into a flask equipped with stirrer, thermometer, feeding funnel, nitrogen purge, and reflux condenser containing 150 ml. of dry benzene. The reaction mixture was refluxed for 3 hours under a very slow nitrogen purge. The reactants were cooled, transferred to a rotary evaporator where the benzene was removed by distillation under vacuum. 42 grams of a slightly yellowish syrup was recovered. After standing for several days, the syrup crystallized into a composition having a paste like consistency. After examination by phosphorus-31 NMR, the sample was found to be a mixture of 20% of $(C_6H_5)_2$—P(O)—P—$(OCH_3)_2$ and about 40% of $(C_6H_5)_2$—P—P$(C_6H_5)_2$.

PREPARATION 4

1.2 grams (0.05 mole) of magnesium was weighed into a 125 ml. flask equipped with magnetic stirrer, thermometer, feeding funnel, $N_2$ purge and reflux condenser. After purging with $N_2$ 50 ml. of tetrahydrofuran was added to the magnesium. The contents were stirred while phenyl dichlorophosphine 8.9 grams (0.05 mole) was fed in dropwise with occasional external cooling with a water bath to maintain a reaction temperature of 50°–60° C. After phosphine addition was completed the contents were stirred at 50° C. for 4 hours. The reaction mixture was cooled to room temperature (25° C.), transferred to a separating funnel and washed with 30 ml. of water. The water was removed and the oil layer was allowed to evaporate in air to about 50% of the original volume. Then a second addition of 30 ml. of water precipitated 2.1 grams of a white solid which, when recrystallized from acetonitrile, gave a product with a melting point of 150° C., consistent with reported literature results. The structure of the compound was determined to be as follows:

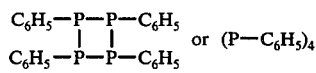

PREPARATION 5

A copolycarbonate of phenolphthalein and Bisphenol A was prepared by condensing 112.5 pounds of Bisphenol A and 37.5 pounds of phenolphthalein with 68 pounds of phosgene. The reaction was carried out in a solution of 1200 pounds of methylene chloride and 162.5 pounds pyridine in a 200 gallon glass-lined Pfaudler reactor. Para tertiary butyl phenol (2.10 pounds) was added as a terminator to control molecular weight.

After polymerization, the pyridine hydrochloride formed in the reaction and any excess pyridine was removed by contacting the polymer solution with a solution of 76 pounds of 12N HCl in 30 gallons of distilled water. An aliquot of the polymer solution in methylene chloride was removed and washed two additional times with 30 volume percent distilled water. The water was separated and removed after each wash. Final traces of water were removed by contacting the solution with silica gel. The polymer solution was then filtered, the polymer precipitated with hexane, and air dried.

The copolycarbonate was about 25 weight percent phenolphthalein and had a molecular weight of about 33,000 weight average molecular weight by gel permeation chromatography.

EXAMPLES 1–4

Stabilization of Polycarbonates

Known quantities of stabilizers prepared as above were blended with the 25 weight percent phenolphthalein copolycarbonate of Preparation 5 using ethanol as the solvent. The polymers were then air dried followed by vacuum drying at 110° C. for 4 hours. One gram of the treated polymers were weighed into a 13 × 100 mm. test tube and purged with nitrogen. The test tubes were inserted into a 1¾ inch deep hole in an aluminum block with the temperature being controlled at 350° C. The heat cycle time was 30 minutes. A nitrogen pad (a pressure of about 3.7 mm. of Hg) was maintained on the samples during the heat cycle.

After the heat cycle, the sample was cooled. The test tube was broken and the polymer was dissolved in methylene chloride. The glass particles were removed by filtration and the filtrate was diluted with more methylene chloride to make up a 100 ml. solution. The color was determined on the solution by using a "Spectronic" Bausch and Lomb Photometer at 350 m$\mu$ and reported in Table I as percent transmittance.

TABLE I

| Examples | Stabilizer used | PPM | Atmosphere | Heat Cycle Time, Min. | Color % Transmittance |
|---|---|---|---|---|---|
| Control 1 | No stabilizer, no heating | — | $N_2$ | — | 97 |
| Control 2 | No stabilizer | — | $N_2$ | 30 | 73 |
| Control 3 | Sandostab P-EPQ$^{TM}$ | 1000 | $N_2$ | 30 | 92 |
| Control 4 | Weston 618$^{TM}$ | 1000 | $N_2$ | 30 | 94 |
| Example 1 | Preparation 1 | 1000 | $N_2$ | 30 | 95 |
| Example 2 | Preparation 2 | 1000 | $N_2$ | 30 | 92 |
| Example 3 | Preparation 3 | 1000 | $N_2$ | 30 | 94 |
| Example 4 | Preparation 4 | 1000 | $N_2$ | 30 | 84 |

Sandostab P-EPQ is the trademark of Sandoz Ltd. and covers the compound tetrakis[2,4-di t-butylphenyl] 4,4'-bisphenylyldiphoshonite.

The foregoing table indicates that the phosphorus to phosphorus compositions of Examples 1–4 are substantially equivalent to the known commercial stabilizers.

EXAMPLE 5

Stabilization of Polyethylene

Blend Preparation

High density polyethylene (5.0 Melt index, 9.962 density) was used as the base resin. A fifteen pound sample was prepared by dryblending 500 parts per million of the Preparation I with the base resin and then double-pass extruding the mixture at 300° C. with a nitrogen purge on the feed hopper of the extruder. The extrustions were done on a 1¼ inch extruder. After blending and extrusions, the sample was analyzed for its melt index.

Multi-Extrusion (Melt Index Stability)

The 15 pound, blended sample was extruded at 500° F. using a 1¼ inch extruder. It is to be noted that the multi-extrusion test at 500° F. is a very severe test when compared to actual processing conditions of a product. After each pass through the extruder, a sample was taken for melt index analysis. A decrease in melt index signified a breaking down and crosslinking of the polymer. The best antioxidant system would show the smallest overall change in melt index. A 15 pound unmodified sample was also extruded at 500° F. to serve as the control.

The melt indexes (gm/10 minutes) were determined using ASTM procedure D-1238.

The following results were obtained on polyethylene containing 500 ppm of the product from Preparation I and polyethylene containing no additive:

| | Melt Index | |
|---|---|---|
| Number of Extrustions | Polyethylene with 500 ppm of Product From Preparation I | Control (Polyethylene with no Additives) |
| Original Blend | 4.92 | 4.89 |
| After 1st Extrusion at 500° F. | 3.18 | 2.76 |
| After 2nd Extrusion at 500° F. | 1.60 | 0.84 |

Similar results are obtained with polypropylene.

EXAMPLE 6

A 300 gram sample of the polycarbonate powder of Preparation 5 was slurried with approximately 2 liters of distilled water in a Waring blender. While the water-polymer slurry was vigorously agitated, a solution of 1.5 grams of 3,9-di(octadecyloxy)-2,4,8,10-tetraoxa-3,9-diphosphaspiro-5,5-undecane (Weston 618 TM) in 15 milliliters of methylene chloride was slowly added. The polycarbonate powder was then collected on a filter and air dried.

This procedure was repeated to add 1.5 grams of the product of Preparation I to 300 grams of polycarbonate to give a blend containing 500 parts per million of Preparation I.

The two samples were vacuum oven dried and injection molded. Optical properties of the clear molded thermoplastic were determined with a Hunterlab D-25 color difference meter. The yellow-index (YI) was determined according to the ASTM-1925-63T procedure.

These two molded polycarbonate samples were placed in a circulating-air oven and heat aged at 120° C. They were removed at various times and the following increase in YI noted from the measured optical properties.

| | YI at Various Times | | | |
|---|---|---|---|---|
| | 0 Days | 2 Days | 3 Days | 7 Days |
| Control | 6.22 | 10.39 | 11.67 | 14.57 |
| Example 6 | 5.51 | 7.91 | 9.02 | 11.74 |

The foregoing data shows that the polycarbonate blend of Example 6 was superior to a commercial stabilizer in the development of a yellow tinge as determined by the yellow index.

Similar results are obtained with polycarbonates derived from bisphenol A and phosgene by techniques well known in the art.

We claim:

1. A composition which comprises a thermoplastic polymer and a stabilizing amount of a compound having one of the formulas $$(R_1)(R_2)P(=X)_1 — P(=X)_a(R_1)(R_2) \quad \text{I}$$

$$(P — R_1)_n \quad \text{II}$$

$$(R_1)(R_2)P(=X)_a — P(R_3) — P(=X)_a(R_1)(R_2) \quad \text{III}$$

wherein $a$ is independently 0 or 1, $n$ is 3 to 6, X is oxygen or sulfur, $R_1$, $R_2$, and $R_3$ are independently dialkylamino, alkoxy, aryloxy, alkyl, aryl, alkaryl, aralkyl, or $R_1$ and $R_2$ taken with the P atom represent a cyclic structure having only carbon, phosphorus and oxygen atoms in the cyclic structure.

2. A composition as set forth in claim 1 wherein the compound has the formula $$(R_1)(R_2)P(=X)_a — P(=X)_a(R_1)(R_2)$$

wherein
$a$ is independently 0 or 1,
X is oxygen or sulfur,
$R_1$, $R_2$ are independently dialkylamino, alkoxy, aryloxy, alkyl, aryl, alkaryl, aralkyl or $R_1$ and $R_2$ taken with the P atom represent a cyclic structure having only carbon, phosphorus and oxygen atoms in the cyclic structure.

3. A composition as set forth in claim 2 wherein the compound has the formula

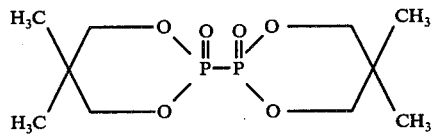

4. A composition as set forth in claim 1 wherein the thermoplastic polymer is a polycarbonate.

5. A composition as set forth in claim 2 wherein the thermoplastic polymer is a polycarbonate.

6. A composition as set forth in claim 3 wherein the thermoplastic polymer is a polycarbonate.

7. A composition as set forth in claim 1 wherein the compound has the formula $$(P — R_1)_n$$

wherein
$R_1$ is dialkylamino, alkoxy, aryloxy, alkyl, aryl, alkaryl, and aralkyl.

8. A composition as set forth in claim 1 wherein the compound has the formula $$(R_1)(R_2)P(=X)_a - P(R_3) - P(=X)_a(R_1)(R_2)$$

wherein
  $a$ is independently 0 or 1,
  X is oxygen or sulfur,
  $R_1$, $R_2$ are independently dialkylamino, alkoxy, aryloxy, alkyl, aryl, alkaryl, aralkyl or
  $R_1$ and $R_2$ taken with the P atom represent a cyclic structure having only carbon, phosphorus and oxygen atoms in the cyclic structure.

9. A composition as set forth in claim 7 wherein the thermoplastic polymer is a polycarbonate.

10. A composition as set forth in claim 8 wherein the thermoplastic polymer is a polycarbonate.

* * * * *

UNITED STATES PATENT AND TRADEMARK OFFICE
CERTIFICATE OF CORRECTION

PATENT NO. : 4,111,899

DATED : September 5, 1978

INVENTOR(S) : J. M. Baggett, et al

It is certified that error appears in the above-identified patent and that said Letters Patent are hereby corrected as shown below:

Col. 4, line 23; change "antioxidents" to --antioxidants--.

Col. 6, line 61; change "bisphenylyldiphoshonite" to --bisphenyldiphosphonite--.

Col. 7, line 5; change "300°C" to --300°F.--.

Col. 7, line 7; change "extrustions" to --extrusions--.

Col. 8, line 18; change "$(=x)_1$" to --$(=x)_a$--.

Signed and Sealed this

Twelfth Day of June 1979

[SEAL]

Attest:

RUTH C. MASON
Attesting Officer

DONALD W. BANNER
Commissioner of Patents and Trademarks